(12) United States Patent
Barduson et al.

(10) Patent No.: US 9,907,488 B2
(45) Date of Patent: Mar. 6, 2018

(54) HIGH INTENSITY PREPARATION, PHYSICAL EXERCISE AND RECOVERY SYSTEM

(71) Applicant: GHB LLC, La Jolla, CA (US)

(72) Inventors: Gene Barduson, San Diego, CA (US); Ted Barduson, San Diego, CA (US)

(73) Assignee: GHB, LLC, La Jolla, CA (US)

( * ) Notice: Subject to any disclaimer, the term of this patent is extended or adjusted under 35 U.S.C. 154(b) by 1009 days.

(21) Appl. No.: 13/923,879

(22) Filed: Jun. 21, 2013

(65) Prior Publication Data

US 2014/0378870 A1 Dec. 25, 2014

(51) Int. Cl.

| A61B 5/107 | (2006.01) |
|---|---|
| A61H 1/00 | (2006.01) |
| A61H 23/02 | (2006.01) |
| G06F 19/00 | (2018.01) |
| A63B 21/00 | (2006.01) |
| A61B 5/00 | (2006.01) |
| A63B 22/00 | (2006.01) |
| A63B 23/04 | (2006.01) |

(52) U.S. Cl.
CPC .......... *A61B 5/1075* (2013.01); *A61H 1/001* (2013.01); *A61H 1/005* (2013.01); *A61H 23/02* (2013.01); *A63B 21/00196* (2013.01); *G06F 19/3481* (2013.01); *A61B 5/4519* (2013.01); *A61B 2503/10* (2013.01); *A63B 22/0076* (2013.01); *A63B 2023/0411* (2013.01)

(58) Field of Classification Search
CPC ........ A61H 23/00; A61H 1/001; A61H 1/005; A61B 5/1075

USPC .................................................. 600/587–595
See application file for complete search history.

(56) References Cited

U.S. PATENT DOCUMENTS

| 2008/0171639 A1* | 7/2008 | Hahn | A61H 1/003 482/52 |
|---|---|---|---|
| 2009/0182204 A1* | 7/2009 | Semler | A61B 5/04085 600/301 |
| 2012/0004570 A1* | 1/2012 | Shimizu | A61B 5/0537 600/547 |
| 2013/0040271 A1* | 2/2013 | Rytky | G09B 19/0038 434/247 |

(Continued)

*Primary Examiner* — Max Hindenburg
*Assistant Examiner* — Jonathan M Foreman
(74) *Attorney, Agent, or Firm* — ARC IP Law, PC; Joseph J. Mayo

(57) ABSTRACT

A high intensity preparation, physical exercise and recovery system configured to prepare muscles for workout through vibration, accept muscular input of high intensity, recover muscles through vibration. Embodiments provide an exercise system that enables a user to obtain a high intensity workout in a small amount of time, for example 15 minutes, and yet increase the user's metabolic rate for hours. Embodiments of the invention may further perform an initial and/or ongoing analysis in terms of body composition analysis and/or extremity composition analysis/score in order to target particular muscles, fat and/or skeletal areas. In one or more embodiments the system may provide outputs including suggested alterations in physical activity and/or food to consume in order to achieve targeted goals for example as compared to the user's trends of change over time, or in comparison to other user's trends down to the granularity of extremities and not just overall body metrics.

6 Claims, 4 Drawing Sheets

(56) References Cited

U.S. PATENT DOCUMENTS

2013/0158368 A1\* 6/2013 Pacione .................. E04F 13/06
                                                        600/301

\* cited by examiner

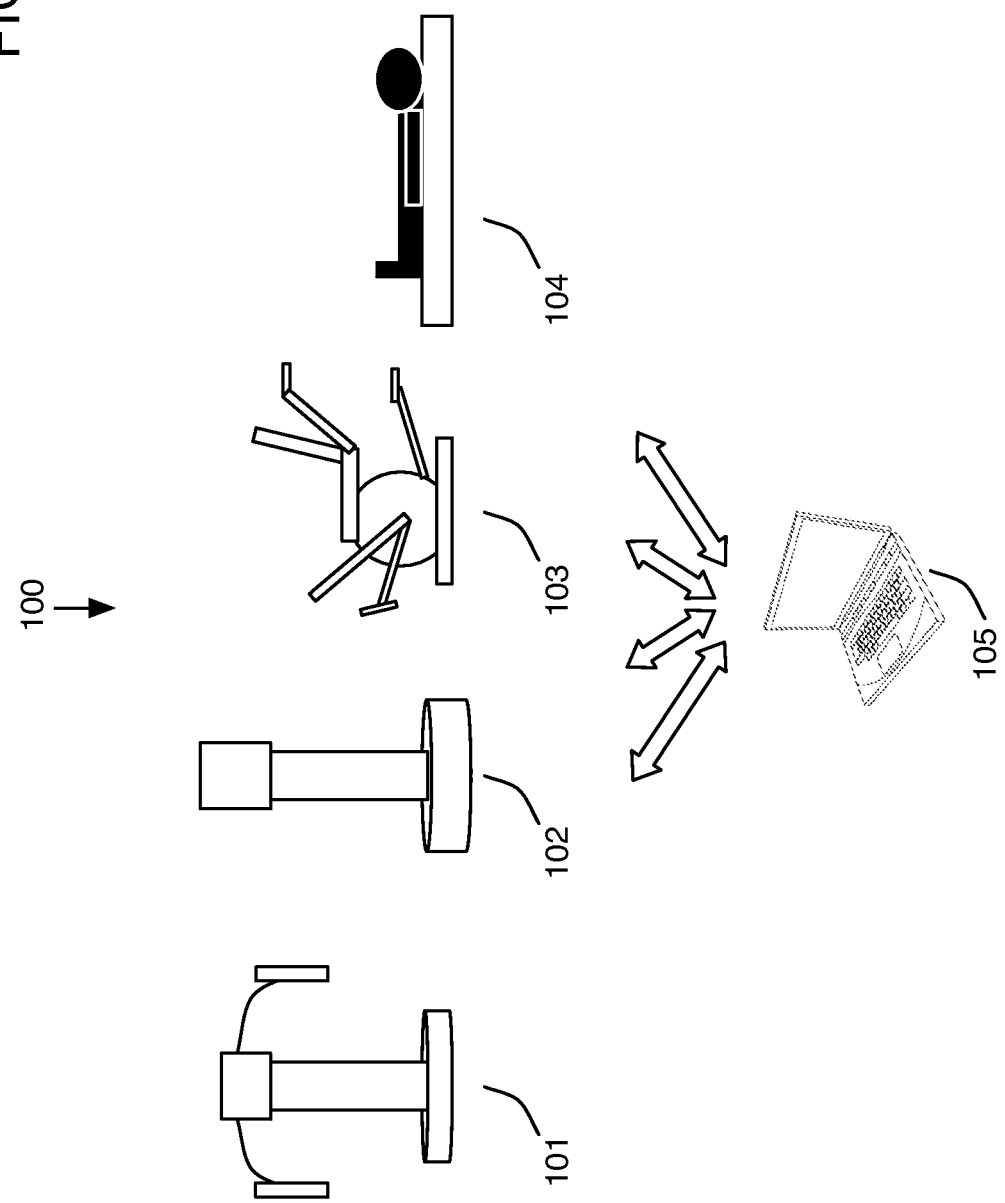

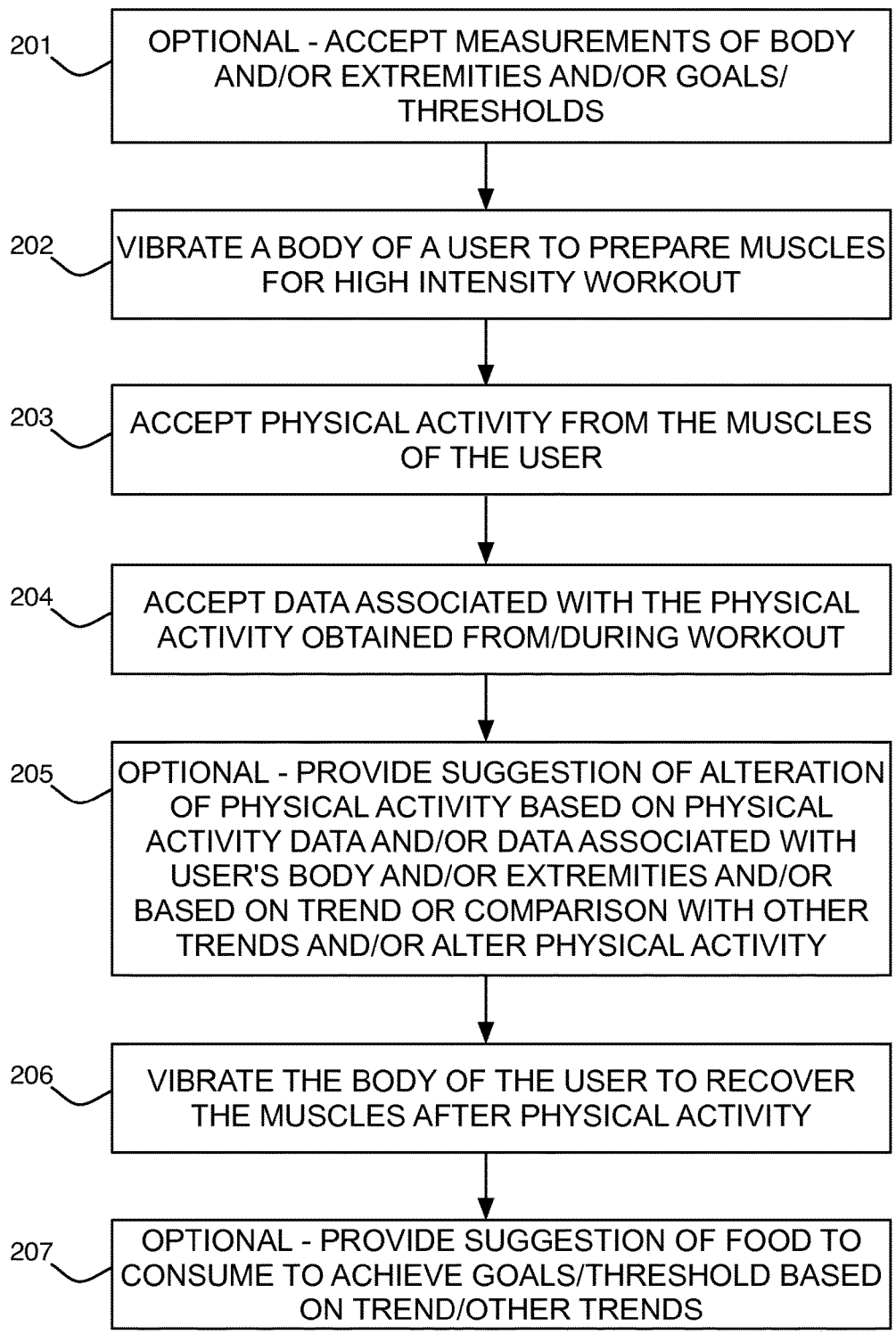

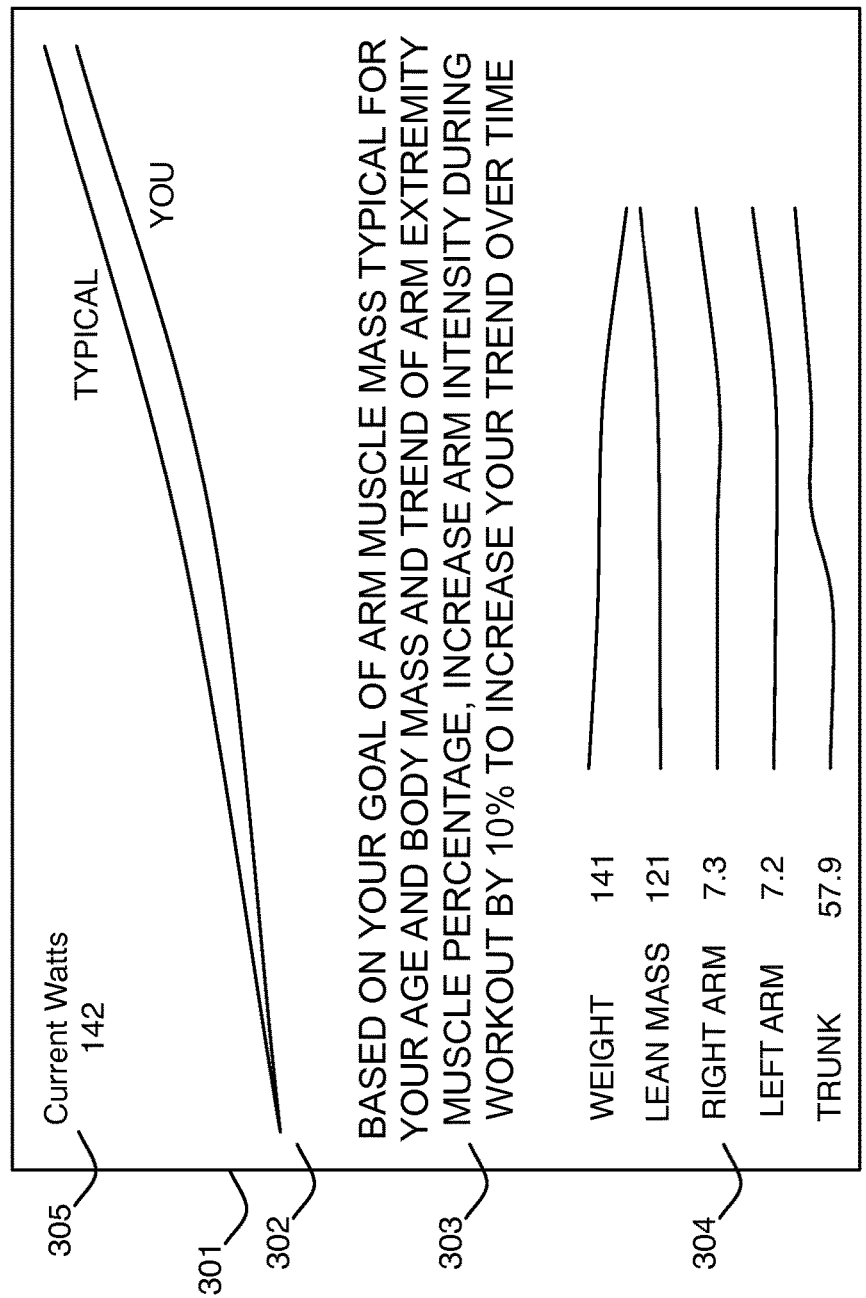

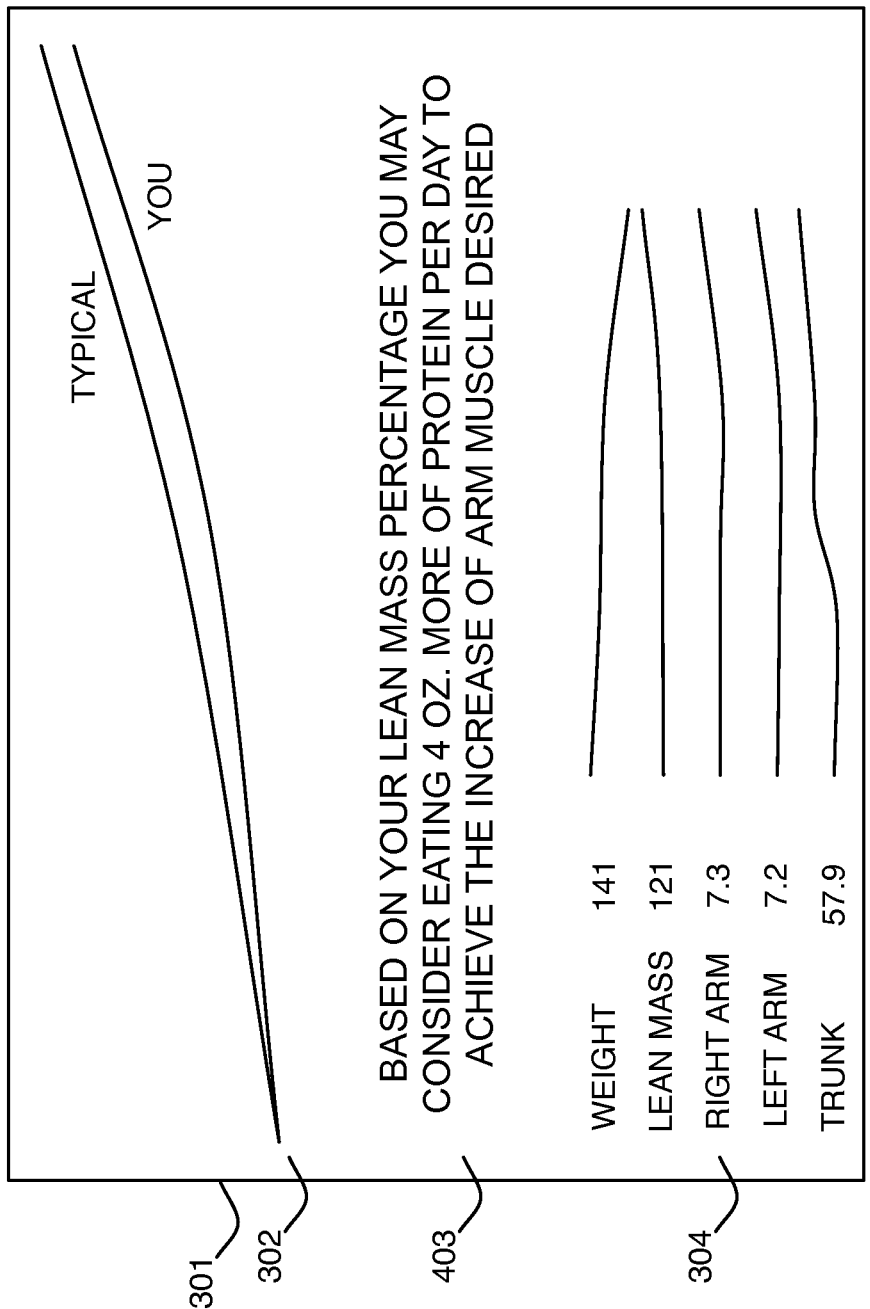

HIGH INTENSITY PREPARATION, PHYSICAL EXERCISE AND RECOVERY SYSTEM

BACKGROUND OF THE INVENTION

Field of the Invention

One or more embodiments of the invention are related to the field of exercise systems. More particularly, but not by way of limitation, one or more embodiments of the invention enable a high intensity preparation, physical exercise and recovery system configured to prepare muscles for workout through vibration, accept muscular input of high intensity, recover muscles through vibration. Embodiments provide an exercise system that enables a user to obtain a high intensity workout in a small amount of time, for example 15 minutes, and yet increase the user's metabolic rate for hours. Embodiments of the invention may further perform an initial and/or ongoing analysis in terms of body composition analysis and/or extremity composition analysis in order to target particular muscles, fat and/or skeletal areas, optionally calculate a score based thereon, and target the high intensity exercise based on the body composition analysis and/or extremity composition analysis and/or score. In one or more embodiments the system may provide outputs including suggested alterations in physical activity and/or food to consume in order to achieve targeted goals for example as compared to the user's trends of change over time, or in comparison to other user's trends down to the granularity of extremities and not just overall body metrics.

Description of the Related Art

Physical exercise as referred to herein relates to wellness and fitness related activity undertaken by the human body. There are many types of exercise that may be broadly categorized by the type of motion and speed at which the motion is undertaken. One taxonomy of exercise includes aerobic exercise, anaerobic exercise and stretching. Aerobic exercising includes activities such as walking, running, biking, for example. Anaerobic exercise includes activities such as lifting weights, interval training and other such activities that utilize more oxygen than can be obtained during the exercise. Stretching related exercises generally are activities that improve the range of motion for various body parts. Regardless of the type of exercise, physical movement is generally acknowledged as an important factor for the physical and mental well being of individuals.

In the agricultural world of old, a large percentage of the population was involved with manual labor on farms for example and hence undertook physical activity on a daily basis in order to earn their livelihood. Obesity was rare, and in addition, the diets of the population included less saturated fat and did not include pesticides or other chemical post processing that is now commonly added to foods to increase sugar, salt and fat content, to increase sales of food. Preservatives were generally unknown at the time, notwithstanding salt drying. The advent of highly efficient farm machinery and industrial jobs that do not require significant manual labor have changed the amount of physical activity that a large percentage of the population achieves. Based on the type food that is currently consumed in the industrialized world and based on the general lack of physical activity, it is predicted that many of the world's children in industrialized nations will succumb to diabetes and other diseases related to inactivity and poor diet. In addition, a large percentage of the adult population work long hours in sedentary jobs and do not allocate a significant amount of time to exercise based on their careers and social obligations. People that do exercise currently require a significant amount of time to achieve a particular level of work effort based on the types of exercise apparatus that are common.

Specifically, apparatus have been developed over the years to enable individuals to move particular body parts to obtain physical exercise and to otherwise counteract the inactivity common in modern industrial life. For example, some people exercise to obtain physical activity to maintain their health, ironically, performing physical activity that used to be obtained through manual labor that people no longer achieve on a large-scale basis in their jobs. Current solutions for exercise generally include a multitude of different types of apparatus designed to exercise one or more body parts. Most apparatus enable exercise of one body part at a time, for example bench press or stationary bicycle to exercise and otherwise "isolate" the chest or legs respectively.

Another type of exercise apparatus includes a vibration apparatus utilized by a Russian scientist to improve the strength and flexibility of athletes in Russia in the 1960's. Modern variations include platforms that a user stands on to in effect perform strength training with their own body weight. Long term use of vibration platforms has not been shown to increase strength relative to static strength exercises as per the placebo-controlled paper of Delecluse et al. (2003), "Strength increase after whole-body vibration compared with resistance training", *Medicine and science in sports and exercise* 35 (6): 1033-41. Hence in general, vibration platforms have been mainly utilized for low stress exercise and for elderly patients that have been bedridden or who experienced bone loss. In general, vibration based exercise alone requires as much time as convention exercise such as walking or other physical activities for example to achieve a particular benefit level.

Other types of exercise apparatus have been designed for rapid workouts, notably the "Range of Motion" machine, or "ROM" machine. This type of machine enables a quick workout but does not prepare the muscles for the workout and does not provide a mechanism for recovering muscles after the workout. Hence, this particular apparatus is another example of a standalone apparatus that fails to address the entire workout process as a whole.

To the point, the main problem with known exercise apparatus is that in general they are utilized in a standalone manner in a time ordered fashion, and not combined in an intelligent manner into a system that prepares a user for high intensity exercise, enables the high intensity exercise and recovers the user's muscles after the high intensity exercise. In addition, known systems do not include accurate analysis capabilities to measure the skeletal muscle mass, percentage of body fat or fat an lean portions of extremities to enable a system to provide recommendations for alterations to high intensity exercise to minimize exercise time and to target particular body parts or extremities that are not within a desired threshold for muscle or to provide recommendations for particular foods to consume to reach target goals. For at least the limitations described above there is a need for a high intensity preparation, physical exercise and recovery system.

BRIEF SUMMARY OF THE INVENTION

One or more embodiments described in the specification are related to a high intensity preparation, physical exercise and recovery system. Embodiments of the system may include a first vibration component configured to vibrate a body of a user for example at a frequency greater than 0.5

Hz to prepare muscles of the body for a high intensity workout, a workout component configured to accept physical activity from the muscles of the user and a second vibration component configured to vibrate the body of the user for example between 0.5 and 50 Hz to recover the muscles after acceptance of the physical activity. The first and second vibration components may be located within the workout component, or separate components. In addition, the first and second vibration components may part of one apparatus or may be the same component that is asserted before and after accepting the physical activity in keeping with the spirit of the invention.

In one or more embodiments, the first vibration component is configured to vibrate the body of the user for at least 3 minutes before the high intensity workout. Other embodiments may utilize more or less vibration time before the high intensity workout as long as the total time of the workout is kept under a predefined time limit, for example 15 minutes. In at least one embodiment, the first vibration component is configured to vibrate feet of the user while the user is standing to activate the muscles of the user before the high intensity workout. Other predefined time limits that are generally short, but longer than 15 minutes may also be utilized in keeping with the spirit of the invention.

The system may utilize any type of physical exercise apparatus capable of accepting high intensity physical activity. In one or more embodiments, the workout component is configured to accept physical activity from the muscles of the user for at least 4 minutes and less than 9 minutes during the high intensity workout. In other embodiments, the workout component may accept more or less time such that the total time including the first and second vibration periods combined with the workout time total a predefined amount, for example 15 minutes. Other time periods that are shorter than static exercise durations associated with sequential time ordered physical activities on differing apparatus is in keeping with the spirit of the invention.

In one or more embodiments, the second vibration component is configured to vibrate the body of the user for at least 5 minutes to recover the muscles after acceptance of the physical activity. The vibration period for recovery may be varied as long as the total time of the workout is kept under a predefined time limit, for example 15 minutes. In at least one embodiment, the second vibration component is configured to vibrate a back portion of the body of the user to lower lactic acid to recover the muscles after acceptance of the physical activity.

One or more embodiments may include a measurement component configured to measure muscle mass and fat mass in the body of the user and in extremities of the user. This enables precise targeting of high intensity training to achieve target goals of the user. This is possible by providing the measurement component and measuring the body muscle and fat mass of the user and the user's extremities over time for example. This component may be utilized once to categorize a user or otherwise analyze a user and/or may be utilized before or during or after each session in keeping with the spirit of the invention.

One or more embodiments of the invention may include a computer configured to accept data associated with the physical activity obtained from the workout component. For example, embodiments of the system may store, e.g., via the computer, the time of the physical activity and/or the level of work performed during the physical activity or both, and may further store the specific body parts or extremities associated with, e.g., that perform the physical activity as accepted by the system.

One or more embodiments of the computer may provide a suggestion of an alteration of the physical activity based numerous factors, for example based on the data associated with the physical activity. For example, embodiments may determine that the level of physical activity currently being performed is below the desired level and display or otherwise inform the user that the level of physical activity should be increased. Alternatively, if the level of physical activity currently being performed is above a desired level, the system may inform the user in a congratulatory manner, or may display or otherwise inform the user that the level of physical activity should be decreased, for example for safety reasons.

One or more embodiments of the computer may accept data associated with the body of the user from the measurement component. Embodiments so configured may also provide a suggestion of an alteration of the physical activity based on the data associated with the body of the user. For example, if the general body fat mass of the user is of a certain level, the computer may provide a suggestion to perform lower intensity physical activity for a longer time, or alternatively provide a suggestion to perform higher intensity physical activity for a shorter time. Other factors may be taken into consideration such as the user's age or trends of performance, or in comparison with other user's trends as discussed below. Embodiments of the computer may also provide a suggestion of a food to consume by the user based on the data associated with the body of the user. For example, if the user has a low muscle mass and high fat mass, the computer may suggest more protein and less fat in the user's diet.

In one or more embodiments the computer may also accept data associated with the physical activity and provide the suggestion of the food to consume by the user based on the data associated with the body of the user and with the data associated with the physical activity. For example, if the user is losing fat mass over time at a rate which may be deemed unhealthy, the system may provide a suggestion for the user to consume slightly more healthy fat to slow the process down to a safe level, for example in conjunction with review by medical professionals.

In one or more embodiments, the computer may accept a first target threshold for the muscle mass and the fat mass in the body of the user and alter an amount of time for the physical activity based on a difference between the first target threshold and the actual muscle mass and the fat mass in the body of the user. In these or other embodiments, the computer may also accept a second target threshold for the muscle mass and the fat mass in the extremities of the user and alter an amount of time of physical activity that is specific to extremities based on a difference between the second target threshold and the actual muscle mass and the fat mass in the extremities of the user. This capability provides a high degree of specificity for muscle mass to ensure for example an overall healthy body including extremities and for example in comparison to the average person of a particular sex and age, or in comparison to an athlete of a particular sex and age or any other data set.

One or more embodiments of the computer may also calculate a trend of muscle mass and fat mass in the body of the user and/or in the extremities of the user over time. The system may also calculate a comparison based on a difference between the trend and with a second trend associated with a second user, alter an amount of time for the physical activity based on the comparison and/or alter an amount of time of physical activity that is specific to extremities based on the comparison.

Embodiments of the invention may utilize all components and functionality detailed herein in combination in keeping with the spirit of the invention.

BRIEF DESCRIPTION OF THE DRAWINGS

The above and other aspects, features and advantages of the invention will be more apparent from the following more particular description thereof, presented in conjunction with the following drawings wherein:

FIG. 1 illustrates an architectural view of at least one embodiment of the high intensity preparation, physical exercise and recovery system.

FIG. 2 illustrates an embodiment of the functionality of the system in flowchart form.

FIG. 3 illustrates an output showing the suggested training changes along with a trend for the user and a comparison thereof between the trend of the user and other users.

FIG. 4 illustrates an output showing the suggest diet to achieve the target results.

DETAILED DESCRIPTION OF THE INVENTION

A high intensity preparation, physical exercise and recovery system will now be described. In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

FIG. 1 illustrates an architectural view of at least one embodiment of the high intensity preparation, physical exercise and recovery system 100. Embodiments of the system may include a first vibration component 102 configured to vibrate a body of a user at a frequency greater than 0.5 Hz to prepare muscles of the body for a high intensity workout, a workout component 103 configured to accept physical activity from the muscles of the user and a second vibration component 104 configured to vibrate the body of the user between 0.5 and 50 Hz to recover the muscles after acceptance of the physical activity for example. The first and second vibration components may be located within the workout component, or separate components. For example in one or more embodiments, the vibration components may be integrated into the workout component, for example in the seat, pedals, or back support or any combination thereof. In this or other embodiments, the first and second vibration components may part of one apparatus or may be the same component that is asserted before and after the physical activity in keeping with the spirit of the invention.

In one or more embodiments, the first vibration component 102 is configured to vibrate the body of the user for at least 3 minutes before the high intensity workout. Other embodiments may utilize more or less vibration time before the high intensity workout as long as the total time of the workout is kept under a predefined time limit, for example 15 minutes. In at least one embodiment, the first vibration component is configured to vibrate feet of the user while the user is standing to activate the muscles of the user before the high intensity workout. In one or more embodiments, the vibration is utilized by the system to lower cortisol and lactic acid in the body, accelerate blood circulation and lymph drainage and increases oxygen uptake by the cells. The vibration creates a stretch reflex in the tendons and stimulates repeated contractions to prepare the body for the high intensity workout phase. The vibrations are also believed to increase balance, coordination, bone density, and lower joint pain and reduce stress in the ligaments and tendons as well. It is also believed that the vibration increases human growth hormone output, serotonin, neurotrophine, testosterone and IGF-1 growth hormones. Vibration in different frequency ranges may be utilized to stimulate different portions of the body. For example, vibration of between 6-7 Hz mainly stimulates the thighs, hamstrings, shoulders and arms, vibration in the range of 8-11 Hz mainly stimulates the thighs, hamstrings mid-section, pectoral muscles, back muscles and shoulders, vibration in the range of 12-16 Hz mainly stimulates the thighs, hamstrings and shoulders, vibration in the range of 17-20 Hz mainly stimulates the thighs, hamstrings and calf muscles, vibration in the range of 21-25 Hz mainly stimulates the hamstrings and stomach muscles, while vibration in the range of 30-35 Hz lightly stimulates the calf muscles, back muscles, shoulders and arms. Although some exercise may be performed while vibration is output, embodiments of the system generally utilize the vibration element to prepare the body for a high intensity workout as opposed to basic exercise during vibration.

The system may utilize any type of physical exercise apparatus 103 capable of accepting high intensity physical activity. In one or more embodiments, the workout component is configured to accept physical activity from the muscles of the user for at least 4 minutes and less than 9 minutes during the high intensity workout. In other embodiments, the workout component may accept more or less time such that the total time including the first and second vibration periods combined with the workout time total a predefined amount, for example 15 minutes. Other time periods that are shorter than static exercise durations associated with sequential time ordered physical activities on differing apparatus is in keeping with the spirit of the invention. In one or more embodiments, the apparatus may utilize any electronic or non-electronic exercise machine, for example a Range of Motion® or "ROM" machine or any other type of apparatus.

Embodiments of the physical exercise apparatus 103 are generally configured to overload the muscles, generally in a high oxygen consumption and/or anaerobic manner. Generally, the amount of time required to overload the cardiovascular system is exponentially reduced with respect to the linear increase in oxygen consumption per unit time. For example, walking for approximately an hour and a half at a relatively low consumption of oxygen per unit time provides approximately the same cardiovascular benefits as sprinting for a few minutes at 7-8 times the consumption of oxygen per unit time. Walking is extremely time consuming, and only a very small percentage of the muscles of the body are utilized at a low range of motion. High intensity exercises, for example that utilize more muscles through a greater range of motion result in an order of magnitude or more of utilization of the muscle cells in the body with respect to walking. In addition, although a very short exercise period is utilized by the system, which consumes few calories, the metabolism of the user is stimulated for hours after the acceptance of the high intensity physical activity by the system. In this manner, a 4 minute workout on a ROM machine for example results in more calories burned by the user that an hour-long walk on a treadmill.

Embodiments of the invention may also utilize any other exercise element that may accept high intensity physical activity such as rowing machines with increased time to account for less muscle utilization than a ROM machine. Alternatively or in combination, exercise machines with less range of motion than a rowing machine may be utilized for an equivalent amount of time, if the number of muscles for example is higher, for example a squat machine. The advantage of a machine that works more muscles through a higher range of motion is that the total time to achieve a particular calorie workout is lowered. For example, 4 minutes of cross training on a ROM machine is equivalent to 20-45 minutes of aerobic exercise for the cardiovascular system and an additional 20-45 minutes of resistance training and an addition 20-45 minutes of stretching. In addition, walking, jogging and running on the other hand may actually damage joints and connective tissue through excessive repetitive motion and impact and is not time efficient while also resulting in loss of upper body mass. Weight training by itself may result in a lowering of flexibility, and provides only limited aerobic results. Yoga and Pilates on the other hand are good for flexibility and toning, but are costly and time consuming with only moderate cardiovascular benefits. Swimming is a good overall exercise for the body, but again is time intensive as is bicycling. Hence, in one or more embodiments a ROM machine is utilized to minimize total time of accepting high intensity physical activity by the system.

In one or more embodiments, the second vibration component 104 is configured to vibrate the body of the user for at least 5 minutes to recover the muscles after acceptance of the physical activity. The vibration period for recovery may be varied as long as the total time of the workout is kept under a predefined time limit, for example 15 minutes. In at least one embodiment, the second vibration component is configured to vibrate a back portion of the body of the user to lower lactic acid to recover the muscles after acceptance of the physical activity. In one or more embodiments, the type of vibration machine may be an TurboSonic® machine, which may be utilized as the first vibration component as well or may be a different machine or type of machine.

One or more embodiments may include a measurement component 101 configured to measure muscle mass and fat mass in the body of the user and in extremities of the user. This enables precise targeting of high intensity training to achieve target goals of the user. This is possible by providing the measurement component and measuring the body muscle and fat mass of the user and the user's extremities over time for example. In one or more embodiments of the system, an InBody® measurement machine may be utilized or any other type of measurement system configured to measure body and/or extremity muscle and fat mass for example. Embodiments of the measurement component may be utilized once for a given user, or at the start of each session with the system or in any other time period. One or more embodiments of the measurement component may also obtain measurements for intracellular and extracellular water, total body water, dry lean mass or any other physiological measurement desired for the particular implementation.

One or more embodiments of the invention may include a computer 105 configured to accept data associated with the physical activity obtained from the workout component. For example, embodiments of the system may store, e.g., via the computer, the time of the physical activity and/or the level of work performed during the physical activity or both, and may further store the specific body parts or extremities associated with, e.g., that perform the physical activity as accepted by the system. In one or more embodiments a passive or active RFID, for example on a key chain may be read by each of the machines as the system vibrates or accepts physical input in order to identify the particular user. In one or more embodiments each of the machines, or elements coupled to the machines may set and or communicate the vibration settings and or workout measurements accepted by the system to computer 105. Alternatively or in combination an assistant may obtain and/or input the vibration settings and input the workout measurements into computer 105 for analysis.

FIG. 2 illustrates an embodiment of the functionality of the system in flowchart form. Embodiments of the computer 105 may accept measurements of the body and/or extremities and/or goals and/or thresholds at 201. The system vibrates the body via vibration component 102 to prepare the muscles for the high intensity workout at 202. The workout component 103 accepts physical activity at 203. The data associated with the workout is accepted by the computer 105 at 204. This may be performed during or after the workout. Based on the workout, a score for work output per extremity or overall body work output may be calculated and utilized to tune the workout in real-time or during the subsequent workout, alone or in combination with any measurement numbers. For example, the computer may provide a suggestion of the alteration of physical activity based on the current or previous physical activity data, data associated with the user's body and/or extremities or trend of metrics of the user over time or in comparison with other users and/or suggest alterations or actually alter the difficulty level for example during the workout at 205. The vibration component 104 vibrates the body of the user to recover the muscles at 206, for example in one embodiment between 6 and 20 Hz although any other previously described frequency range may be utilized for example to reduce cortisol and lactic acid and otherwise reduce soreness for example. The computer may also provide suggested food to consume to achieve goals based on the physical data activity and/or trend of the user's metrics whether physical activity performance level or body or extremity metrics and/or in comparison with other user's trends at 207.

FIG. 3 illustrates an output 301 showing the suggested training changes 303 along with a trend for the user 302 and a comparison thereof between the trend of the user and other users. For example, one or more embodiments of the computer may provide a suggestion of an alteration of the physical activity based numerous factors, for example based on the data associated with the physical activity, e.g., the wattage of the current physical activity shown at area 305. For example, embodiments may determine that the level of physical activity currently being performed is below the desired level and display or otherwise inform the user that the level of physical activity should be increased. Alternatively, if the level of physical activity currently being performed is above a desired level, the system may inform the user in a congratulatory manner, or may display or otherwise inform the user that the level of physical activity should be decreased, for example for safety reasons. Any other trends of any other physiology parameters whether measured by measurement component 101 or calculated in any other manner for a particular user or group of users may also be plotted or otherwise displayed in keeping with the spirit of the invention.

One or more embodiments of the computer may accept data associated with the body of the user from the measurement component and display the metrics at 304 for example. Embodiments so configured may also provide a suggestion of an alteration of the physical activity based on the data associated with the body of the user, or extremities as well. For example, if the general body fat mass of the user is of a certain level, the computer may provide a suggestion to perform lower intensity physical activity for a longer time, or alternatively provide a suggestion to perform higher intensity physical activity for a shorter time. Other factors may be taken into consideration such as the user's age or trends of performance, or in comparison with other user's trends as discussed below.

FIG. 4 illustrates an output showing the suggest diet 403 to achieve the target results. Embodiments of the computer may also provide a suggestion of a food to consume by the user based on the data associated with the body of the user. For example, if the user has a low muscle mass and high fat mass, the computer may suggest more protein and less fat in the user's diet. In one or more embodiments the computer may also accept data associated with the physical activity and provide the suggestion of the food to consume by the user based on the data associated with the body of the user and with the data associated with the physical activity. For example, if the user is losing fat mass over time at a rate which may be deemed unhealthy, the system may provide a suggestion for the user to consume slightly more healthy fat to slow the process down to a safe level, for example in conjunction with review by medical professionals.

In one or more embodiments, the computer may accept a first target threshold for the muscle mass and the fat mass in the body of the user and alter an amount of time for the physical activity based on a difference between the first target threshold and the actual muscle mass and the fat mass in the body of the user. In these or other embodiments, the computer may also accept a second target threshold for the muscle mass and the fat mass in the extremities of the user and alter an amount of time of physical activity that is specific to extremities based on a difference between the second target threshold and the actual muscle mass and the fat mass in the extremities of the user. This capability provides a high degree of specificity for muscle mass to ensure for example an overall healthy body including extremities and for example in comparison to the average person of a particular sex and age, or in comparison to an athlete of a particular sex and age or any other data set.

One or more embodiments of the computer may also calculate a trend of muscle mass and fat mass in the body of the user and/or in the extremities of the user over time. The system may also calculate a comparison based on a difference between the trend and with a second trend associated with a second user, alter an amount of time for the physical activity based on the comparison and/or alter an amount of time of physical activity that is specific to extremities based on the comparison.

Embodiments of the invention may utilize all components and functionality detailed herein in combination in keeping with the spirit of the invention.

While the invention herein disclosed has been described by means of specific embodiments and applications thereof, numerous modifications and variations could be made thereto by those skilled in the art without departing from the scope of the invention set forth in the claims.

What is claimed is:

1. A high intensity preparation, physical exercise and recovery system comprising:
   a measurement component configured to measure data associated with a body of a user comprising actual muscle mass and actual fat mass in the body of the user and in extremities of the user;
   a first vibration component configured to vibrate the body of the user at a frequency greater than 0.5 Hz for a first predetermined time period before acceptance of physical activity from the user comprising a high intensity workout to prepare muscles of the body for the high intensity workout,
      wherein said first predetermined time period is at least 3 minutes, and
      wherein said measurement component is configured to measure muscle mass and fat mass in the body of the user and in extremities of the user before said first vibration component vibrates the body of the user;
   a workout component configured to accept the physical activity from the muscles of the user for a second predetermined time period, wherein said second time period is at least 4 minutes and less than 9 minutes during the high intensity workout;
   a second vibration component configured to vibrate the body of the user between 5 and 20 Hz for a third predetermined time period to recover the muscles after acceptance of the physical activity that is asserted after the second predetermined time period of physical activity,
      wherein said second vibration component is a separate and distinct component than said first vibration component,
      wherein the third predetermined time period is at least 5 minutes,
      wherein the first vibration component is configured to vibrate feet of the user while the user is standing to activate the muscles of the user before the high intensity workout, and
      wherein the second vibration component is configured to vibrate a back portion of the body of the user to lower lactic acid to recover the muscles after acceptance of the physical activity; and,
   a computer configured to accept data associated with the physical activity from the workout component; and
      accept the data associated with the body of the user from the measurement component before said first vibration component vibrates the body of the user.

2. The high intensity preparation, physical exercise and recovery system of claim 1, wherein
   the computer is further configured to
      provide a suggestion of an alteration of the physical activity based on the data associated with the physical activity after said acceptance of the physical activity from the user; and
      provide a suggestion of an alteration of the physical activity after said acceptance of the physical activity from the user based on the data associated with the body of the user accepted before said first vibration component vibrates the body of the user.

3. The high intensity preparation, physical exercise and recovery system of claim 1, wherein
   the computer is further configured to
      provide a suggestion of a food to consume by the user based on the data associated with the body of the user accepted before said first vibration component vibrates the body of the user or with the data associated with the physical activity after said acceptance of the physical activity from the user.

4. The high intensity preparation, physical exercise and recovery system of claim 1, wherein
the computer is further configured to
accept a first target threshold for muscle mass and fat mass in the body of the user, or
accept a second target threshold for muscle mass and fat mass in the extremities of the user, or
accept both the first and second target thresholds; and,
alter the amount of time for the physical activity based on a difference between the first target threshold and the actual muscle mass and the actual fat mass in the body of the user measured via the measurement component, or
alter the amount of time of physical activity that is specific to the extremities based on a difference between the second target threshold and the actual muscle mass and the actual fat mass in the extremities of the user measured via the measurement component, or
alter both the amount of time for the physical activity and the amount of time of physical activity that is specific to the extremities.

5. The high intensity preparation, physical exercise and recovery system of claim 1, wherein
the computer is further configured to
calculate a trend of muscle mass and fat mass in the body of the user and in the extremities of the user over time;
calculate a comparison based on a difference between the trend and with a second trend associated with a second user;
alter an amount of time for the physical activity based on the comparison; and,
alter an amount of time of physical activity that is specific to the extremities based on the comparison.

6. A high intensity preparation, physical exercise and recovery system comprising:
a measurement component configured to measure data associated with a body of a user comprising actual muscle mass and actual fat mass in the body of the user and in extremities of the user;
a first vibration component configured to vibrate the body of the user at a frequency greater than 0.5 Hz for a first predetermined time period before acceptance of physical activity from the user comprising a high intensity workout to prepare muscles of the body for the high intensity workout,
wherein said first predetermined time period is at least 3 minutes, and wherein said measurement component is configured to measure muscle mass and fat mass in the body of the user and in extremities of the user before said first vibration component vibrates the body of the user;
a workout component configured to accept the physical activity from the muscles of the user for a second predetermined time period, wherein said second predetermined time period is at least 4 minutes and less than 9 minutes during the high intensity workout;
a second vibration component configured to vibrate the body of the user between 5 and 20 Hz for a third predetermined time period to recover the muscles after acceptance of the physical activity that is asserted after the physical activity,
wherein said second vibration component is a separate and distinct component than said first vibration component, wherein the third predetermined time period is at least 5 minutes, wherein the first vibration component is configured to vibrate feet of the user while the user is standing to activate the muscles of the user before the high intensity workout, and
wherein the second vibration component is configured to vibrate a back portion of the body of the user to lower lactic acid to recover the muscles after acceptance of the physical activity;
a computer configured to accept data associated with the body of the user from the measurement component before said first vibration component vibrates the body of the user; provide a suggestion of an alteration of the physical activity based on data associated with the physical activity after acceptance of the physical activity from the user and before said second vibration component vibrates the body of the user; provide a suggestion of an alteration of the physical activity based on the data associated with the body of the user after acceptance of the physical activity and before said second vibration component vibrates the body of the user; accept a first target threshold for muscle mass and fat mass in the body of the user, or accept a second target threshold for muscle mass and fat mass in the extremities of the user, or accept both the first and second target thresholds; and,
alter the amount of time for the physical activity based on a difference between the first target threshold and the actual muscle mass and the actual fat mass in the body of the user, or
alter the amount of time of physical activity that is specific to the extremities based on a difference between the second target threshold and the actual muscle mass and the actual fat mass in the extremities of the user, or alter both the amount of time for the physical activity and the amount of time of physical activity that is specific to the extremities; and, calculate a trend of muscle mass and fat mass in the body of the user and in the extremities of the user over time; calculate a comparison based on a difference between the trend and with a second trend associated with a second user;
alter an amount of time for the physical activity based on the comparison; and, alter an amount of time of physical activity that is specific to the extremities based on the comparison.

* * * * *